US007199197B2

(12) United States Patent
Caldwell et al.

(10) Patent No.: US 7,199,197 B2
(45) Date of Patent: Apr. 3, 2007

(54) WATER- AND OIL-REPELLENT FLUOROACRYLATES

(75) Inventors: Gregg A. Caldwell, Cottage Grove, MN (US); John C. Clark, White Bear Lake, MN (US); David J. Kinning, Woodury, MN (US); Alan R. Kirk, Cottage Grove, MN (US); Thomas P. Klun, Lakeland, MN (US); Ramesh C. Kumar, Maplewood, MN (US); Roger A. Mader, Stillwater, MN (US); George G. I. Moore, Afton, MN (US); Zai-Ming Qiu, Woodbury, MN (US); Richard B. Ross, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 43 days.

(21) Appl. No.: 11/027,604

(22) Filed: Dec. 28, 2004

(65) Prior Publication Data
US 2005/0143541 A1 Jun. 30, 2005

Related U.S. Application Data

(60) Provisional application No. 60/534,203, filed on Dec. 31, 2003.

(51) Int. Cl.
C08F 12/20 (2006.01)

(52) U.S. Cl. ............ 526/242; 526/286; 526/319; 528/70; 524/544; 560/167

(58) Field of Classification Search .......... 526/242, 526/286, 319; 528/28, 70; 524/544; 560/167
See application file for complete search history.

(56) References Cited

U.S. PATENT DOCUMENTS

| | | | |
|---|---|---|---|
| 2,803,615 A | 8/1957 | Ahlbrecht et al. | |
| 3,011,988 A | 12/1961 | Luedke et al. | |
| 3,278,352 A | 10/1966 | Erickson | |
| 3,282,905 A | 11/1966 | Fasick et al. | |
| 3,318,852 A | 5/1967 | Dixon | |
| 3,378,609 A | 4/1968 | Fasick et al. | |
| 3,398,182 A | 8/1968 | Guenthner et al. | |
| 3,413,226 A | 11/1968 | Coleman | |
| 3,455,889 A | 7/1969 | Coleman | |
| 3,458,391 A | 7/1969 | Miller, Jr. | |
| 3,459,834 A | 8/1969 | Schmitt | |
| 3,787,351 A | 1/1974 | Olson | |
| 4,321,404 A | 3/1982 | Williams et al. | |
| 4,366,300 A | 12/1982 | Delescluse | |
| 4,513,059 A | 4/1985 | Dabroski | |
| 4,778,915 A | 10/1988 | Lina et al. | |
| 4,792,444 A | 12/1988 | Fukasawa et al. | |
| 4,920,190 A | 4/1990 | Lina et al. | |
| 5,032,460 A | 7/1991 | Kantner et al. | |
| 5,093,398 A | 3/1992 | Rottger et al. | |
| 5,115,059 A | 5/1992 | Le | |
| 5,144,056 A | 9/1992 | Lina et al. | |
| 5,173,547 A | 12/1992 | Rottger et al. | |
| 5,446,118 A | 8/1995 | Shen et al. | |
| 5,688,884 A | 11/1997 | Baker et al. | |
| 5,723,630 A | 3/1998 | Cheburkov et al. | |
| 5,725,789 A * | 3/1998 | Huber et al. | 252/8.62 |
| 5,872,180 A | 2/1999 | Michels et al. | |
| 5,883,175 A | 3/1999 | Kubo et al. | |
| 6,001,923 A | 12/1999 | Moncur et al. | |
| 6,114,045 A | 9/2000 | Juhue et al. | |
| 6,197,378 B1 | 3/2001 | Clark et al. | |
| 6,265,060 B1 | 7/2001 | Arudi et al. | |
| 6,482,911 B1 | 11/2002 | Jariwala et al. | |

(Continued)

FOREIGN PATENT DOCUMENTS

EP  0 712 046 A1  5/1996

(Continued)

OTHER PUBLICATIONS

G. Oertel, Polyurethane Handbook, (1993), 2$^{nd}$ Edition, Hanser/Gardner Publications, Inc., Cincinnati, OH.

(Continued)

*Primary Examiner*—David W. Wu
*Assistant Examiner*—M. Bernshteyn
(74) *Attorney, Agent, or Firm*—Lisa P. Fulton

(57) ABSTRACT

Fluoroacrylates comprise the reaction product of:
(a) at least one fluorochemical alcohol represented by the formula:

$$C_nF_{2n+1}\text{—X—OH}$$

wherein:

n = 1 to 4,

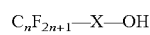

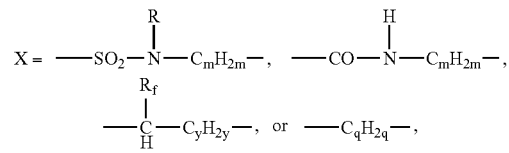

R=hydrogen or an alkyl group of 1 to 4 carbon atoms,
m=2 to 8,
$R_f = C_nF_{2n+1}$,
y=0 to 6, and
q=1 to 8;
(b) at least one unbranched symmetric diisocyanate; and
(c) at least one hydroxy-terminated alkyl (meth)acrylate or 2-fluoro acrylate monomer having 2 to about 30 carbon atoms in its alkylene portion.

43 Claims, No Drawings

U.S. PATENT DOCUMENTS

| | | |
|---|---|---|
| 6,500,439 B1 | 12/2002 | Morita et al. |
| 6,569,521 B1 | 5/2003 | Sheridan et al. |
| 6,664,354 B2 | 12/2003 | Savu et al. |
| 6,750,277 B1 | 6/2004 | Yamana et al. |
| 6,803,109 B2 * | 10/2004 | Qiu et al. ............. 428/423.1 |
| 6,890,360 B2 | 5/2005 | Cote et al. |
| 6,939,580 B2 | 9/2005 | Enomoto et al. |
| 2001/0005738 A1 | 6/2001 | Bruchmann et al. |
| 2003/0001130 A1 | 1/2003 | Qiu |
| 2003/0026997 A1 | 2/2003 | Qiu et al. |
| 2003/0083448 A1 | 5/2003 | Fan et al. |
| 2003/0130457 A1 | 7/2003 | Maekawa et al. |
| 2004/0147188 A1 | 7/2004 | Johnson et al. |
| 2005/0106326 A1 | 5/2005 | Audenaert et al. |
| 2005/0137289 A1 | 6/2005 | Hooftman et al. |
| 2005/0143595 A1 | 6/2005 | Klun et al. |

FOREIGN PATENT DOCUMENTS

| | | |
|---|---|---|
| EP | 0 849 392 A2 | 6/1998 |
| EP | 1 225 187 A1 | 7/2002 |
| EP | 1 225 188 A1 | 7/2002 |
| EP | 1 329 548 A1 | 7/2003 |
| EP | 1 380 628 A1 | 1/2004 |
| FR | 1.468.301 | 12/1966 |
| GB | 870022 | 6/1961 |
| GB | 1120304 | 7/1968 |
| JP | 61-148208 | 7/1986 |
| WO | WO 97/14842 A1 | 4/1997 |
| WO | WO 01/30873 | 5/2001 |
| WO | WO 03/048224 A1 | 6/2003 |
| WO | WO 03/062521 A1 | 7/2003 |
| WO | WO 2005/06224 A1 | 7/2005 |
| WO | WO 2005/065164 A2 | 7/2005 |

OTHER PUBLICATIONS

U.S. Appl. No. 11/027,633, filed Dec. 28, 2004, entitled "Water- and Oil-Repellent Fluorourethanes and Fluoroureas".

U.S. Appl. No. 11/027,612, filed Dec. 28, 2004, entitled "Fluoroacrylate-Multifunctional Acrylate Copolymer Compositions".

U.S. Appl. No. 11/027,605, filed Dec. 28, 2004, entitled "Fluoroacrylate-Mercaptofunctional Copolymers".

U.S. Appl. No. 11/027,606, filed Dec. 28, 2004, entitled "Water-Based Release Coating Containing Fluorochemical".

U.S. Appl. No. 11/027,602, filed Dec. 28, 2004, entitled "Fluorochemical Containing Low Adhesion Backsize".

* cited by examiner

WATER- AND OIL-REPELLENT FLUOROACRYLATES

CROSS REFERENCE TO RELATED APPLICATION

This application claims priority to U.S. Provisional Patent Application No. 60/534,203, filed Dec. 31, 2003.

FIELD

This invention relates to water- and oil-repellent fluoroacrylate monomers and polymers.

BACKGROUND

Various fluorinated acrylic resins containing urethane linkages are known to have oil and water repellency properties (see, for example, U.S. Pat No. 4,321,404 (Williams et al.), U.S. Pat. No. 4,778,915 (Lina et al.), U.S. Pat. No. 4,920,190 (Lina et al.), U.S. Pat. No. 5,144,056 (Anton et al.), and U.S. Pat. No. 5,446,118 (Shen et al.)). These resins can be polymerized and applied as coatings to substrates such as, for example, textiles, carpets, wall coverings, leather, and the like to impart water- and oil repellency.

Typically, these resins comprise long chain pendant perfluorinated groups (for example, 8 carbon atoms or greater) because long chains readily align parallel to adjacent pendant groups attached to acrylic backbone units, and thus maximize water- and oil-repellency. However, long chain perfluorinated group-containing compounds such as, for example, perfluorooctyl containing compounds may bioaccumulate in living organisms (see, for example, U.S. Pat. No. 5,688,884 (Baker et al.)).

SUMMARY

In view of the foregoing, we recognize that there is a need for polymerizable water- and oil-repellent acrylic resins that are less bioaccumulative.

Briefly, in one aspect, the present invention provides water- and oil-repellent fluoroacrylates that have short chain perfluorinated groups (5 carbon atoms or less), which are believed to be less toxic and less bioaccumulative than longer chain perfluorinated groups (see, for example, WO 01/30873). The fluoroacrylates of the invention comprise the reaction product of:

(a) at least one fluorochemical alcohol represented by the formula:

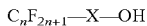

wherein:

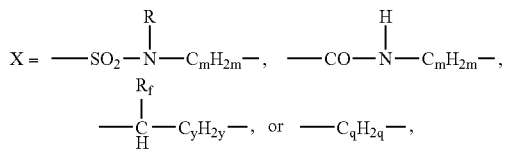

R=hydrogen or an alkyl group of 1 to 4 carbon atoms,
m=2 to 8,
$R_f = C_n F_{2n+1}$,
y=0 to 6, and
q=1 to 8;

(b) at least one unbranched symmetric diisocyanate; and
(c) at least one hydroxy-terminated alkyl (meth)acrylate or 2-fluoroacrylate monomer having 2 to about 30 carbon atoms in its alkylene portion.

As used herein, the term "(meth)acrylate monomer" refers to both acrylate monomers and methacrylate monomers.

The invention also provides fluoroacrylates represented by the following general formula:

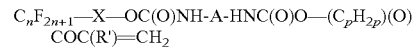

wherein:

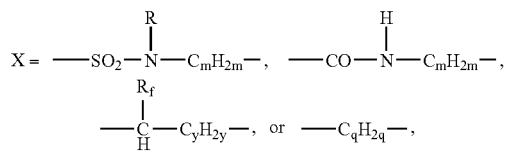

R=H or an alkyl group of 1 to 4 carbon atoms,
m=2 to 8,
$R_f = C_n F_{2n+1}$,
y=0 to 6,
q=1 to 8,
A=an unbranched symmetric alkylene group, arylene group, or aralkylene group,
p=2 to 30, and
R'=H, $CH_3$, or F.

It has been discovered that the fluoroacrylates of the invention exhibit good water- and oil-repellency properties. In light of the prior art, one would expect that fluoroacrylates derived from shorter perfluorinated chains would not be as effective at imparting water- and oil-repellency as those derived from longer perfluorinated chains (see, for example, U.S. Pat. No. 2,803,615 (Ahlbrecht et al.) and U.S. Pat. No. 3,787,351 (Olson)). Surprisingly, however, the fluoroacrylates of the invention exhibit water- and oil-repellency comparable to fluoroacrylates with longer perfluorinated chains.

The fluoroacrylates of the invention therefore meet the need in the art for polymerizable water- and oil-repellent acrylic resins that are less bioaccumulative.

In another aspect, this invention provides fluorinated isocyanates that are useful in making the fluoroacrylates of the invention. The fluorinated isocyanates can be represented by the following general formula:

wherein:
n=1 to 5,

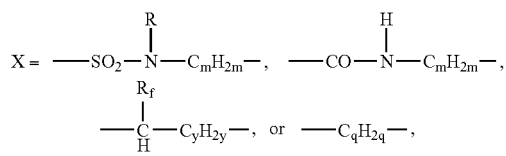

R=H or an alkyl group of 1 to 4 carbon atoms,
m=2 to 8,
$R_f = C_n F_{2n+1}$, y=0 to 6, q=1 to 8, and A=an unbranched symmetric alkylene group, arylene group, or aralkylene group.

In other aspects, this invention also provides fluorinated acrylic polymers comprising repeating units of the fluoroacrylates of the invention, coating compositions and release coating compositions comprising the fluorinated acrylic polymers, and articles coated with the coating or release coating compositions.

DETAILED DESCRIPTION

Fluorochemical alcohols that are useful in the fluoroacrylates of the invention can be represented by the formula:

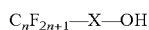

wherein:

n = 1 to 5,

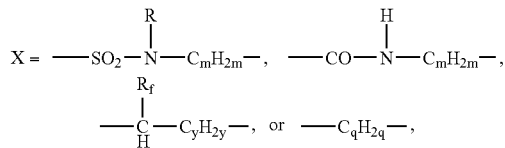

R=hydrogen or an alkyl group of 1 to 4 carbon atoms, m=2 to 8, $R_f = C_n F_{2n+1}$, y=0 to 6, and q=1 to 8.

Representative examples of suitable alcohols include $CF_3CH_2OH$, $(CF_3)_2CHOH$, $(CF_3)_2CFCH_2OH$, $C_2F_5SO_2NH(CH_2)_2OH$, $C_2F_5SO_2NCH_3(CH_2)_2OH$, $C_2F_5SO_2NCH_3(CH_2)_4OH$, $C_2F_5SO_2NC_2H_5(CH_2)_6OH$, $C_2F_5(CH_2)_4OH$, $C_2F_5CONH(CH_2)_4OH$, $C_3F_7SO_2NCH_3(CH_2)_3OH$, $C_3F_7SO_2NH(CH_2)_2OH$, $C_3F_7CH_2OH$, $C_3F_7CONH(CH_2)_8OH$, $C_4F_9(CH_2)_2OH$, $C_4F_9SO_2NCH_3(CH_2)_2OH$, $C_4F_9CONH(CH_2)_2OH$, $C_4F_9SO_2NCH_3(CH_2)_4OH$, $C_4F_9SO_2NH(CH_2)_7OH$, $C_4F_9SO_2NC_3H_7(CH_2)_2OH$, $C_4F_9SO_2NC_4H_9(CH_2)_2OH$, $C_5F_{11}SO_2NCH_3(CH_2)_2OH$, $C_5F_{11}CONH(CH_2)_2OH$, and $C_5F_{11}(CH_2)_4OH$.

Preferably, n is 1 to 4; more preferably, n is 4. Preferably, m is 2 to 4. Preferably, q is 2.

Preferably, X is

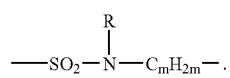

More preferably, X is

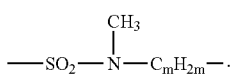

Most preferably, X is selected from the group consisting of

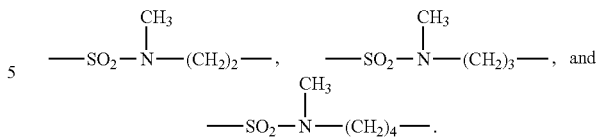

Preferred fluorochemical alcohols include, for example, $C_4F_9SO_2NCH_3(CH_2)_2OH$, $C_4F_9SO_2NCH_3(CH_2)_4OH$, and $C_4F_9(CH_2)_2OH$. A more preferred fluorochemical alcohol is $C_4F_9SO_2NCH_3(CH_2)_2OH$.

Symmetric diisocyanates are diisocyanates that meet the three elements of symmetry as defined by *Hawley's Condensed Chemical Dictionary* 1067 (1997). First, they have a center of symmetry, around which the constituent atoms are located in an ordered arrangement. There is only one such center in the molecule, which may or may not be an atom. Second, they have a plane of symmetry, which divides the molecule into mirror-image segments. Third, they have axes of symmetry, which can be represented by lines passing through the center of symmetry. If the molecule is rotated, it will have the same position in space more than once in a complete 360° turn.

As used herein, the term "unbranched" means that the symmetric diisocyanate does not contain any subordinate chains of one or more carbon atoms.

Representative examples of unbranched symmetric diisocyanates include 4,4'-diphenylmethane diisocyanate (MDI), 1,6-hexamethylene diisocyanate (HDI), 1,4-phenylene diisocyanate (PDI), 1,4-butane diisocyanate (BDI), 1,8-octane diisocyanate (ODI), 1,12-dodecane diisocyanate, and 1,4-xylylene diisocyanate (XDI).

Preferred unbranched symmetric diisocyanates include, for example, MDI, HDI, and PDI. A more preferred unbranched symmetric diisocyanate is MDI. In its pure form, MDI is commercially available as Isonate™ 125M from Dow Chemical Company (Midland, Mich.), and as Mondur™ from Bayer Polymers (Pittsburgh, Pa.).

Hydroxy-terminated alkyl (meth)acrylate and 2-fluoroacrylate monomers that are useful in the fluoroacrylates of the invention can have from 2 to about 30 carbon atoms (preferably, from 2 to about 12 carbon atoms) in their alkylene portion.

Preferably, the hydroxy-terminated alkyl (meth)acrylate monomer is a hydroxy-terminated alkyl acrylate. Preferred hydroxy-terminated alkyl acrylates include, for example, hydroxy ethyl acrylate, hydroxy butyl acrylate, hydroxy hexyl acrylate, hydroxy decyl acrylate, hydroxy dodecyl acrylate, and mixtures thereof.

The fluoroacrylates of the invention can be prepared, for example, by first combining the fluorochemical alcohol and the unbranched symmetric diisocyanate in a solvent, and then adding the hydroxy-terminated alkyl (meth)acrylate. Useful solvents include esters (for example, ethyl acetate), ketones (for example, methyl ethyl ketone), ethers (for example, methyl-tert-butyl ether), and aromatic solvents (for example, toluene).

Preferably, the reaction mixture is agitated. The reaction can generally be carried out at a temperature between room temperature and about 120° C. (preferably, between about 50° C. and about 70° C.).

Typically the reaction is carried out in the presence of a catalyst. Useful catalysts include bases (for example, tertiary amines, alkoxides, and carboxylates), metal salts and chelates, organometallic compounds, acids and urethanes. Preferably, the catalyst is an organotin compound (for example, dibutyltin dilaurate (DBTDL) or a tertiary amine (for example, diazobicyclo[2.2.2]octane (DABCO)), or a combination thereof. More preferably, the catalyst is DBTDL.

When fluorochemical alcohols represented by the formula $C_nF_{2n+1}SO_2NCH_3(CH_2)_mOH$, wherein n=2 to 5, and m=2 to 4, are reacted with MDI, the process described in U.S. patent application Ser. No. 10/751,142, entitled "Process For Preparing Fluorochemical Monoisocyanates," filed on Dec. 31, 2003, can be used.

Fluoroacrylates of the invention can be represented by the following general formula:

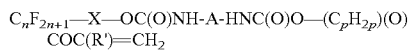

wherein:

n = 1 to 5,

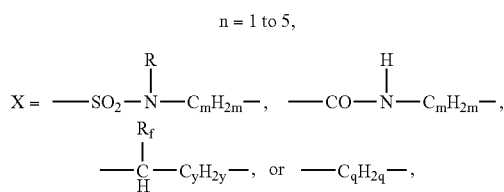

R=H or an alkyl group of 1 to 4 carbon atoms,
m=2 to 8,
$R_f=C_nF_{2n+1}$,
y=0 to 6,
q=1 to 8,
A=an unbranched symmetric alkylene group, arylene group, or aralkylene group,
p=2 to 30, and
R'=H, $CH_3$, or F.

Preferably, n is 1 to 4; more preferably, n is 4. Preferably, q is 2.

Preferably, X is

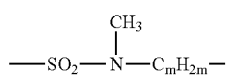

and m is 2 to 4.

Preferably, A is selected from the group consisting of $-C_6H_{12}-$,

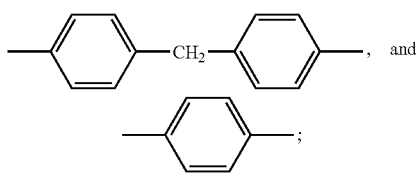

more preferably, A is

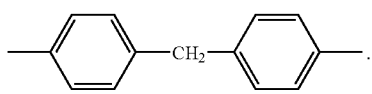

Preferably, p is 2 to 12; more preferably, p is selected from the group consisting of 2, 4, 6, 10, and 12; most preferably, p is 2.

Preferably, R' is H.

Fluoroacrylates of the invention can be polymerized to yield a fluorinated acrylic polymer. Fluorinated acrylic polymers comprising repeating units of fluoroacrylates of the invention exhibit water- and oil-repellency properties.

Fluoroacrylates of the invention can also be copolymerized with one or more nonfunctional comonomers and/or functional comonomers.

Nonfunctional comonomers such as, for example, alkyl acrylates can improve durability and film-forming properties. Representative examples of useful nonfunctional comonomers include methyl (meth)acrylate, butyl acrylate, isobutyl (meth)acrylate, hexyl acrylate, dodecyl acrylate, and octadecyl acrylate. Nonfunctional comonomers can typically be copolymerized with the fluoroacrylates of the invention in about up to a 1:1 molar ratio.

Functional comonomers can provide properties such as, for example, adhesion, hydrophilicity, reactivity, or low glass transition temperatures. Groups that are useful in functional comonomers include, for example, hydroxy, carboxy, quaternary ammonium, acetate, pyrrolidine, polyethylene glycol, sulfonic acid, trialkoxysilane, and silicone. These groups can generally be introduced into the polymer at less than about 20 weight percent (preferably, less than about 5 weight percent). Useful functional comonomers include, for example, acrylic acid, methacrylic acid, N-vinyl 2-pyrrolidinone, and hydroxypropyl acrylate.

Fluoroacrylates of the invention can also be polymerized with methacrylate functional polydimethyl siloxanes such as, for example, methacryloxy propyl polydimethyl silicone, to prepare fluorinated acrylic/siloxane graft copolymers.

Fluorinated acrylic polymers of the invention can be used in coating compositions to impart water- and oil-repellency to a wide variety of substrates. The coating compositions comprise a fluorinated acrylic polymer of the invention and a solvent (for example, water and/or an organic solvent). When the solvent is water, the coating composition typically further comprises a surfactant.

The fluorinated acrylic polymers of the invention can be dissolved, suspended, or dispersed in a wide variety of solvents to form coating compositions suitable for coating onto a substrate. The coating compositions can generally contain from about 0.1 about 10 percent fluorinated acrylic polymer (preferably about 1 to about 5 percent), based on the weight of the coating composition.

The coating compositions can be applied to a wide variety of substrates such as, for example, fibrous substrates and hard substrates. Fibrous substrates include, for example, woven, knit, and nonwoven fabrics, textiles, carpets, leather, and paper. Hard substrates include, for example, glass, ceramic, masonry, concrete, natural stone, man-made stone, grout, metals, wood, plastics, and painted surfaces.

The coating compositions can be applied to a substrate (or articles comprising a substrate) by standard methods such as, for example, spraying, padding, dipping, roll coating, brushing, or exhaustion. Optionally, the composition can be dried to remove any remaining water or solvent.

Polymers and copolymers of the invention can be used for release coatings. Comonomers that are useful in release coatings include, for example, octadecyl acrylate, N-vinyl 2-pyrrolidinone, methacryloxy propyl dimethyl siloxane, acrylic acid, methacrylic acid, acrylonitrile and methyl acrylate. The release coating compositions may or may not require a curing step after coating on a substrate.

Coating compositions useful for release coatings can be applied to surfaces requiring release properties from adhesives. Substrates suitable for release coatings include, for example, paper, metal sheets, foils, non-woven fabrics, and films of thermoplastic resins such as polyesters, polyamides, polyolefins, polycarbonates, and polyvinyl chloride.

Release coating compositions can be applied to suitable substrates by conventional coating techniques such as, for example, wire-wound rod, direct gravure, offset gravure, reverse roll, air-knife, and trailing blade coating. The resulting release coating compositions can provide effective release for a wide variety of pressure sensitive adhesives such as, for example, natural rubber based adhesives, silicone based adhesives, acrylic adhesives, and other synthetic film-forming elastomeric adhesives.

EXAMPLES

Objects and advantages of this invention are further illustrated by the following examples, but the particular materials and amounts thereof recited in these examples, as well as other conditions and details, should not be construed to unduly limit this invention.

| Designator | Name, Formula and/or Structure | Availability |
|---|---|---|
| A-174 | $CH_2=C(CH_3)CO_2C_3H_6Si(OMe)_3$ | Sigma Aldrich, Milwaukee, WI |
| AA | Acrylic acid; $HOC(O)CH=CH_2$ | Sigma Aldrich |
| BA | Butyl acrylate; $C_4H_9OC(O)CH=CH_2$ | Sigma Aldrich |
| DBTDL | Dibutyltin dilaurate | Sigma Aldrich |
| DDA | Dodecyl acrylate; $CH_3(CH_2)_{11}OC(O)CH=CH_2$ | Sigma Aldrich |
| DDSH | Dodecylthiol; $CH_3(CH_2)_{11}SH$ | Sigma Aldrich |
| DMF | Dimethyl formamide | Sigma Aldrich |
| HDI | 1,6-Hexane diisocyanate $OCN(CH_2)_6NCO$ | Sigma Aldrich |
| HEA | Hydroxyethyl acrylate; $HOCH_2CH_2OC(O)CH=CH_2$ | Sigma Aldrich |
| HEMA | Hydroxyethyl methacrylate; $HOCH_2CH_2OC(O)C(CH_3)=CH_2$ | Sigma Aldrich |
| HOBA | Hydroxybutyl acrylate; $HO(CH_2)_4OC(O)CH=CH_2$ | Nippon Kasei Chemical Co., Tokyo. |
| HOPA | Hydroxypropyl acrylate; isomer mixture; $HOCH(CH_3)CH_2OC(O)CH=CH_2$ and $HOCH_2CH(CH_3)OCOCH=CH_2$ | Sigma Aldrich |
| H12MDI | "DESMODUR W" 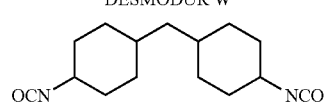 | Bayer Polymers LLC, Pittsburgh, PA |
| IOA | Isooctyl acrylate; i-$C_8H_7OC(O)CH=CH_2$ | 3M, St Paul, MN |

-continued

| Designator | Name, Formula and/or Structure | Availability |
|---|---|---|
| IPDI | Isophorone diisocyanate; | Sigma-Aldrich |
| MA | Methyl acrylate; $CH_3OC(O)CH=CH_2$ | Sigma-Aldrich |
| MAA | Methacrylic acid; $HOCH(O)CCH_3=CH_2$ | Sigma-Aldrich |
| MDI | 4,4'-Methylenebis (phenyl isocyanate); | Sigma-Aldrich |
| MEK | Methyl ethyl ketone; $CH_3C(O)C_2H_5$ | Sigma-Aldrich |
| ODA | Octadecyl acrylate; $CH_3(CH_2)_{17}OC(O)CH=CH_2$ | Sigma-Aldrich |
| PDI | 1,4-Phenylene diisocyanate; | Sigma-Aldrich |
| Phenothiazine | | Sigma-Aldrich |
| TDI | 2,4-Toluene diisocyanate; | Sigma-Aldrich |
| TMXDI | Tetramethylene diisocyanate; | American Cyanamid |
| "VAZO 67" | NCC(Me)(Et)N=NC(Me)(Et)CN | DuPont, Wilmington, DE |

Preparation of HOHA (6-Hydroxyhexyl acrylate)

118 g (1 mol; available from Sigma-Aldrich) 1,6-hexanediol, 36 g (0.5 mol; available from Sigma-Aldrich) AA, 1.0 g p-toluenesulfonic acid hydrate (available from Sigma-Aldrich), 0.016 g phenothiazine, 0.055 g hydroquinone monomethyl ether (available from Sigma-Aldrich) and 300 ml heptane was stirred at reflux in a 3 necked 1-L round bottom flask equipped with a modified Dean-Stark trap.

After 5 hr at reflux, 8.4 ml (0.47 mol) water had collected. Upon cooling, two layers formed. The top layer contained hexanediol diacrylate and heptane. The bottom layer (141.2 g) was analyzed by gas liquid chromatography (GLC) after derivatization with TFAA (trifluoroacetic anhydride available from Aldrich) as 13.9% unreacted diol, 11.0% desired monoacrylate, and a trace of diacrylate. The lower layer was dissolved in 100 ml ethyl acetate and washed three times with 100 ml of water, stripped to 55.7 g, 15% diol, 84% monoacrylate (HOHA), and 1% diacrylate. To the above prepared HOHA mixture (19 g), 100 ml ethyl acetate was added and this solution was washed three times with 150 ml water. The last wash gave an emulsion, which was frozen and thawed to give two phases. The organic phase yielded HOHA (50.1 g red liquid; 99% pure).

Preparation of HOHMA (HO(CH$_2$)$_6$OC(O)C(CH$_3$)=CH$_2$)

HOHMA was prepared essentially according to the procedure described for HOHA with the exception that an equimolar amount of MAA is substituted for AA.

Preparation of HODDA
(12-Hydroxydodecylacrylate)

In a similar fashion to the preparation of HOHA, 203 g (1.0 mol) dodecane-1,12-diol, 36.0 g (0.50 mol), 1.0 g AA, 0.018 g phenothiazine, 0.034 hydroquinone monomethyl ether, and 350 ml heptane were heated at reflux 3.5 hr, and then allowed to cool and form a slurry. Filtration yielded 147.0 g solid (96% diol by GLC analysis). The filtrant was stripped to 120 g of an oil, 2% diol, 80% monoacrylate, and 18% diacrylate. Flash chromatography of 29.5 g from hexane-ethyl acetate 85–15 (vol %) on 257 g 280-400 mesh silica gel (available from Sigma-Aldrich) yielded pure HODDA (17.1 g).

Preparation of C$_4$F$_9$SO$_2$NH(CH$_3$)

C$_4$F$_9$SO$_2$NH(CH$_3$) was prepared by essentially following the procedure described in U.S. Pat. No. 6,664,354 (Savu et al.), Example 1, Part A.

Preparation of MeFBSE: C$_4$F$_9$SO$_2$N(CH$_3$)CH$_2$CH$_2$OH

MeFBSE was prepared by essentially following the procedure described in U.S. Pat. No. 6,664,354 (Savu et al.), Example 2, Part A.

Preparation of MeFESE: C$_2$F$_5$SO$_2$N(CH$_3$)CH$_2$CH$_2$OH

MeFESE was prepared by essentially following the procedure described in U.S. Pat. No. 6,664,354 (Savu et al.), Example 2, Part A with the exception that C$_2$F$_5$SO$_2$F (prepared essentially as described in U.S. Pat. No. 5,723,630) was used as a starting material.

Preparation of MeFBSEA: C$_4$F$_9$SO$_2$N(CH$_3$)CH$_2$CH$_2$OC(O)CH=CH$_2$

MeFBSEA was prepared by essentially following the procedure described in U.S. Pat. No. 6,664,354 (Savu et al.) Example 2, Part A & B.

Preparation of MeFESEA: C$_2$F$_5$SO$_2$N(CH$_3$)CH$_2$CH$_2$OC(O)CH=CH$_2$

A round bottom flask charged with 16.0 g (0.0623 mol) C$_2$F$_5$SO$_2$N(CH$_3$)(CH$_2$)$_2$OH, 33.8 g ethyl acetate, and 10.47 g (0.0810mol) diisopropylethyl amine was placed in an ice bath and cooled to 7 C. The reaction was fitted with a pressure equalizing addition funnel under nitrogen containing 7.33 g (0.0810 mol) acryloyl chloride which was added to the reaction over 12 min. At 200 min, 16.9 g more ethyl acetate was added to the reaction, which was sequentially washed with 30 g 2% aqueous hydrochloric acid and 5% aqueous sodium bicarbonate, dried over anhydrous magnesium sulfate, filtered and concentrated on a rotary evaporator at 55° C. under aspirator pressure to provide 11.93 g crude product. A 7 cm diameter chromatographic column was filled with 230 g of silica gel (#SX1043U-3, grade 62, 60–200 mesh, from EM Science, Darmstadt, Germany) slurried with 60:40 by volume heptane:ethyl acetate and 11.93 g of the product was chromatographed using the column to provide after concentration 7.06 g desired product.

Preparation of C$_8$F$_{17}$SO$_2$NMeC$_2$H$_4$OC(O)CH=CH$_2$ (MeFOSEA)

MeFOSEA was prepared essentially as described in U.S. Pat. No. 6,664,354 (Savu et al.) example 1A and example 2A and 2B with the exception that C$_8$F$_{17}$SO$_2$F (available from Sigma-Aldrich) was used instead of C$_4$F$_9$SO$_2$F.

Preparation of C$_4$F$_9$(CH$_2$)$_2$OC(O)CH=CH$_2$

In a manner similar to the preparation of C$_2$F$_5$SO$_2$N(CH$_3$)(CH$_2$)$_2$OC(O)CH=CH$_2$, 11.02 g (0.0417 mol) C$_4$F$_9$(CH$_2$)$_2$OH (available from TCI America, Portland Oreg.) and 7.01 g (0.0542 mol) diisopropylethyl amine in 22.94 g diethyl ether was reacted with 4.91 g (0.0542 mol) acryloyl chloride over 2 h, washed sequentially washed with 30 g 2% aqueous hydrochloric acid and 5% aqueous sodium bicarbonate, dried over anhydrous magnesium sulfate, filtered and concentrated on a rotary evaporator in a room temperature bath at aspirator pressure to provide a crude product. This was combined with a similar preparation of C$_4$F$_9$(CH$_2$)$_2$OC(O)CH=CH$_2$ made using the same ratios of starting materials, starting with 8.0 g C$_4$F$_9$(CH$_2$)$_2$OH to provide about 25 g of crude product. To these combined products was added 0.005 g p-methoxy phenol and 0.0013 g phenothiazine, and the material was distilled under aspirator pressure at a head temperature of 67 C to provide 8.88 g of the desired product.

Preparation of EOSH: (CH$_3$(OCH$_2$CH$_2$)$_n$OC(O)CH$_2$SH)

A 500 mL three-necked round bottom flask was charged with 25.96 g of CH$_3$(OCH$_2$CH$_2$)$_n$OH(MW=550; 47.20 mmol; available from Sigma-Aldrich), 4.35 g HSCH$_2$CO$_2$H (47.28 mmol; available from Sigma-Aldrich), 2 drops of CF$_3$SO$_3$H catalyst, and 120 mL toluene. The mixture was heated to reflux under nitrogen at 115–120° C. with a mechanical stirrer for 8 hours. Water was removed by azeotropic distillation. Fourier Transform Infrared Spectroscopy (FTIR) analysis indicated the formation of EOSH. The solvent was stripped using a rotary evaporator (27.60 g).

Preparation of $C_4F_9SO_2N(CH_3)C_2H_4OC(O)$
$NHC_6H_4CH_2C_6H_4NCO$(MeFBSE-MDI)

A one liter, three-necked round bottom flask, fitted with a heater, nitrogen inlet, reflux condenser and thermocouple was charged with MeFBSE (357.0 g; 1.0 mole) and MEK (600 mL) and heated to reflux, while distilling out 30 mL of MEK. The mixture was then cooled to 30° C. and treated with MDI (750 g; 3.0 mole). The temperature of the mixture was then increased to about 40° C. for 4 hours, filtered and added to toluene (4 l). The resulting off white precipitate was collected by filtration, and re-crystallized from toluene (white solid; 689.4 g; 57% yield). Structure was confirmed using liquid chromatography/mass spectroscopy (LC/MS) and LC/UV analysis.

Preparation of $C_4F_9SO_2N(CH_3)C_2H_4OC(O)$
$NHC_6H_4CH_2C_6H_4NHCOOCH_2CH_2OC(O)$
$CH=CH_2$(MeFBSE-MDI-HEA)

A one L flask containing 500 mL ethyl acetate was heated to reflux under $N_2$, and 100 mL of ethyl acetate was distilled out. The remaining solvent was cooled under dry air and treated with 151.9 g MeFBSE-MDI, 29.1 g 2-hydroxyethyl acrylate, 2 drops DBTDL, and 7 mg phenothiazine. After 5 hr at 50° C., infrared spectroscopy indicated complete conversion of the isocyanate. The cloudy solution was filtered through 40 g diatomaceous earth and rinsed with hot ethyl acetate to give 473.5 g clear solution, (29.6% solids, yield as MeFBSE-MDI-HEA, 77%).

Preparation of $C_2F_5SO_2N(CH_3)CH_2CH_2OC(O)$
$NHC_6H_4CH_2C_6H_4NCO$ (MeFESE-MDI)

To a flask containing 37.5 g (0.15 mol) MDI in 75 g heptane that was filtered at 50° C. through a C porosity frit, to which was added two drops of DBTDL at 50 C was added 25.7 g (0.10 mol) $C_2F_5SO_2N(CH_3)CH_2CH_2OH$ dropwise over 58 min. At 3.5 h, the resulting solid was filtered, rinsed with 120 g heptane, and vacuumed dry under nitrogen to provide 69.43 g of a white powder that was 71% solids, the remainder being heptane. (49.29 g yield, 97.2%)

Preparation of $C_2F_5SO_2N(CH_3)CH_2CH_2OC(O)$
$NHC_6H_4CH_2C_6H_4NHCOOCH_2CH_2OC(O)$
$CH=CH_2$ (MeFESE-MDI-HEA)

A 250 mL round bottom equipped with overhead stirrer was charged with 40 g of MeFESE-MDI (71% solids, 0.056 mol), 100 g ethyl acetate, 2 drops of dibutylin dilaurate and heated to 50 C in a heating bath under nitrogen. Then 6.50 g (0.056 mol) hydroxyethylacrylate was added in one portion, followed by 6.3 mg of p-methoxy phenol. The bath temperature was adjusted to 60° C. and the reaction ran for 14 h. The reaction was allowed to cool to room temperature over two days, and an absence of the isocyanate peak at 2281 cm−1 was noted by FTIR. Phenothiazine (2 mg) was added to the reaction mixture which was then concentrated in a 55° C. bath at aspirator pressure to yield 35.3 g of a white solid.

The product was dissolved in 10 g ethyl acetate, and chromatographed on a 7 cm diameter chromatographic column filled with 230 g of silica gel (#SX1043U-3, grade 62, 60–200 mesh, from EM Science, Darmstadt, Germany) slurried with 50:50 by volume heptane:ethyl acetate to yield 20.13 g of product.

Preparation of $C_4F_9(CH_2)_2OC(O)$
$NHC_6H_4CH_2C_6H_4NCO$ ($C_4F_9(CH_2)_2OH$-MDI)

$C_4F_9(CH_2)_2OH$-MDI was prepared in a manner similar to the preparation of MeFESE-MDI except that 17.7 g (0.071 moles) of MDI in 30 g of heptane was reacted with 12.5 g (0.047 moles) of $C_4F_9(CH_2)_2OH$.

Preparation of $C_4F_9(CH_2)_2OC(O)$
$NHC_6H_4CH_2C_6H_4NHCOOCH_2CH_2OC(O)$
$CH=CH_2$($C_4F_9(CH_2)_2$(OH-MDI-HEA)

$C_4F_9(CH_2)_2OH$-MDI-HEA was prepared in a manner similar to the preparation of MeFESE-MDI-HEA except that 12.0 g (0.023 mole) of $C_4F_9(CH_2)_2OH$-MDI was reacted with 2.71 g (0.023 mole) of hydroxyethyl acrylate in 40 g of ethyl acetate with DBTDL, followed by workup and chromatography to provide 5.8 g of product.

Preparation of $CF_3CH_2OC(O)$
$NHC_6H_4CH_2C_6H_4NCOOCH_2CH_2OC(O)CH=CH_2$
($CF_3CH_2OH$-MDI-HEA)

A mixture of 33.0 g $CF_3CH_2OH$ (available from Aldrich), 125 g MDI, 2 drops DBTDL and 400 g heptane was stirred at 50° C. 20 hr, filtered while still hot, and the collected solid recrystallized from toluene to give 100 g of $CF_3CH_2OH$-MDI adduct. A solution of 7.0 g of the adduct, 2.32 g HEA, 1 drop DBTDL, and 30 mL dry THF was heated under $N_2$ for 20 hr at about 60° C. Acetone (40 mL) was added to the resultant white slurry, a small amount of insoluble material was filtered and the solution was stripped to 7.6 g white solid. Flash chromatography with 80/20 Hexane/ethyl acetate (v/v) on 200 g silica gel (280–400 mesh, Aldrich) gave 4.1 g pure monomer.

Preparation of poly-MeFBSE-MDI-HEA

A 125 ml bottle was charged with 6.0 g MeFBSE-MDI-HEA, 70 mg "VAZO 67", and 24 g ethyl acetate. After purging with nitrogen for 35 seconds, the bottle was kept in a rotating water bath at 60° C. for 15 hr. The resulting slurry was treated with about 50 ml methanol, filtered and the solid was dispersed in 43 g ethyl acetate. On heating, the solid dissolved, and upon cooling, some solid precipitated. Addition of 6.0 g DMF gave complete solution.

General Procedure for Examples and Comparative Examples Listed in Table 1 & 2.

For each example and comparative example, a 125 ml bottle was charged with 3.0–6.0 g of the fluoroacrylate listed in the table (prepared essentially as described above for MeFBSE-MDI-HEA), 15–40 mg "VAZO 67", and sufficient ethyl acetate to yield a 25–30% by weight concentration of monomer. Appropriate amounts of co-monomers were added to arrive at the wt % listed in Table 2. After purging with nitrogen for 35–60 seconds, the bottle was kept in a rotating water bath at 60° C. for 24–48 hrs. The product often precipitated upon cooling. In some cases the resulting polymer solution was poured into 300–400 mL of methanol. The precipitated polymer was subsequently dispersed in ethyl acetate to yield a 20–30 wt. % solution of polymer. On heating, the solid dissolved and upon cooling, some solid usually precipitated. Addition of small amounts of DMF gave complete solution.

Dynamic Contact Angle Measurement

A test solution, emulsion, or suspension (typically at about 3% solids) was applied to nylon 66 film (available from DuPont) by dip-coating strips of the film. Prior to coating the film was cleaned with methyl alcohol. Using a small binder clip to hold one end of the nylon film, the strip was immersed in the treating solution, and then withdrawn slowly and smoothly from the solution. The coated strip was allowed to air dry in a protected location for a minimum of 30 minutes and then was cured for 10 minutes at 150° C.

Advancing and receding contact angles on the coated film were measured using a CAHN Dynamic Contact Angle Analyzer, Model DCA 322 (a Wilhelmy balance apparatus equipped with a computer for control and data processing, commercially available from ATI, Madison, Wis.). Water and hexadecane were used as probe liquids. Values for both water and hexadecane are reported.

Larger values of contact angles are indicative of better repellency.

TABLE 1
Examples 1–16 and Comparative Examples C1–C11

| Ex. | Fluoroacrylate Composition | Contact Angle in degrees Advancing (Receding) Water | Hexadecane |
|---|---|---|---|
| 1 | MeFBSE-HDI-HOHA | 124(93) | 82(68) |
| 2 | MeFBSE-HDI-HODDA | 125(100) | 79(65) |
| 3 | MeFBSE-MDI-HEA | 132(101) | 91(55) |
| 4 | MeFBSE-MDI-HEMA | 123(87) | 81(64) |
| 5 | MeFBSE-MDI-HOPA | 121(86) | 72(63) |
| 6 | MeFBSE-MDI-HOBA | 121(94) | 79(69) |
| 7 | MeFBSE-MDI-HOHA | 129(106) | 83(70) |
| 8 | MeFBSE-MDI-HOHMA | 122(79) | 72(65) |
| C1 | MeFBSE-IPDI-HEA | 111(67) | 66(35) |
| C2 | MeFBSE-IPDI-HEMA | 112(69) | 65(32) |
| C3 | MeFBSE-IPDI-HOHA | 113(65) | 69(33) |
| C4 | MeFBSE-H12MDI-HOHA | 116(63) | 62(37) |
| C5 | MeFBSE-TDI-HEA | 117(80) | 69(61) |
| C6 | MeFBSE-TDI-HEMA | 115(79) | 67(58) |
| C7 | MeFBSE-TDI-HOHA | 121(58) | 71(56) |
| C8 | MeFBSE-TDI-HODDA | 106(67) | 42(26) |
| 9 | MeFBSE-PDI-HEA | 120(100) | 98(55) |
| 10 | MeFBSE-PDI-HEMA | 120(92) | 73(61) |
| 11 | MeFBSE-PDI-HOBA | 120(94) | 83(62) |
| 12 | MeFBSE-PDI-HOHA | 120(97) | 82(67) |
| 13 | MeFBSE-PDI-HODDA | 138(101) | 86(56) |
| C9 | MeFBSE-TMXDI-HEA | 111(55) | 60(39) |
| 14 | $C_4F_9(CH_2)_2$OH-MDI-HEA | 125(86) | 75(66) |
| C10 | $C_4F_9(CH_2)_2$OC(O)CH=CH$_2$ | 127(51) | 83(39) |
| 15 | MeFESE-MDI-HEA | 117(79) | 68(59) |
| C11 | MeFESEA | 112(67) | 62(43) |
| 16 | $CF_3CH_2$OH-MDI-HEA | 121(70) | 72(45) |

TABLE 2
Examples 17–37 and Comparative Example C12

| Ex. | Fluoroacrylate/Comonomer Composition (wt %) | Contact Angle in degrees Advancing (Receding) Water | Hexadecane |
|---|---|---|---|
| 17 | MeFBSE-HDI-HOHA (80) DDA (20) | 123(90) | 81(63) |
| 18 | MeFBSE-MDI-HEA (95) MA (5) | 128(111) | 81(69) |
| 19 | MeFBSE-MDI-HEA (89.4) MA (10.6) | 125(105) | 79(72) |
| 20 | MeFBSE-MDI-HEA (79.4) MA (21.6) | 120(81) | 76(69) |
| 21 | MeFBSE-MDI-HEA (90) BA (10) | 125(105) | 80(69) |
| 22 | MeFBSE-MDI-HEA (80) BA (20) | 120(97) | 78(68) |
| 23 | MeFBSE-MDI-HEA (90) IOA (10) | 124(101) | 81(70) |
| 24 | MeFBSE-MDI-HEA (80) IOA (20) | 125(100) | 79(63) |
| 25 | MeFBSE-MDI-HEA (70) IOA (30) | 122(92) | 79(64) |
| 26 | MeFBSE-MDI-HEA (80) ODA (20) | 123(95) | 78(67) |
| 27 | MeFBSE-MDI-HEA (70) ODA (30) | 128(92) | 81(66) |
| 28 | MeFBSE-MDI-HEA (60) ODA (40) | 127(91) | 80(68) |
| 29 | MeFBSE-MDI-HEA (50) ODA (50) | 124(101) | 78(72) |
| 30 | MeFBSE-MDI-HEA (75) MeFBSEA (25) | 119(91) | 77(66) |
| 31 | MeFBSE-MDI-HOBA (75) DDA (25) | 93(79) | 82(70) |
| 32 | MeFBSE-MDI-HODDA (75) DDA (25) | 123(95) | 82(40) |
| C12 | MeFBSE-TDI-HODDA (75) DDA (25) | 118(68) | 71(24) |
| 33 | MeFBSE-PDI-HEA (80) ODA (20) | 116(85) | 80(70) |
| 34 | MeFBSE-PDI-HOBA (80) ODA (20) | 107(79) | 80(68) |
| 35 | MeFBSE-PDI-HOHA (80) ODA (20) | 108(80) | 82(67) |
| 36 | MeFBSE-PDI-HODDA (80) ODA (20) | 108(88) | 80(69) |
| 37 | MeFESE-MDI-HEA (70) ODA (30) | 119(109) | 47(37) |

Example 38

Preparation of MeFBSE-MDI-HEA/ODA/AA; 70/26/4

A 125 mL bottle with a magnetic stirrer was charged with 9.46 g 37% MeFBSE-MDI-HEA solution in ethyl acetate (3.50 g solid; 4.84 mmol), 1.30 g ODA (4.005 mmol), 0.2 g AA (2.78 mmol), 28.55 g ethyl acetate and 0.050 g "VAZO-67". The solution was bubbled with nitrogen for two minutes. The sealed bottle was put in a 70° C. oil bath and stirred for 24 hours.

Example 39

Preparation of MeFBSE-MDI-HEA/ODA/A-174 in Ratio of 70/26/4

In a 125 mL bottle with a magnetic stirrer was charged with 9.46 g 37% MeFBSE-MDI-HEA solution in ethyl acetate (3.50 g solid, 4.84 mmol), 1.30 g ODA (4.005 mmol), 0.2 g A-174 (0.805 mmol), 26.84 g ethyl acetate and 0.050 g "VAZO-67". The solution was bubbled with nitrogen for two minutes. The sealed bottle was put in a 70° C. oil bath and stirred for 24 hours.

TABLE 3

Examples 38–39

| Ex. | Fluoroacrylate/Comonomer Composition (wt %) | Contact Angle in degrees Advancing (Receding) | |
|---|---|---|---|
| | | Water | Hexadecane |
| 38 | MeFBSE-MDI-HEA (70) ODA (26) AA (4) | 125(87) | 80(67) |
| 39 | MeFBSE-MDI-HEA (70) ODA (26) A-174 (4) | 119(95) | 81(67) |

Example 40

Preparation of MeFBSE-MDI-HEA/EOSH; 3.0/1.0

A 125 mL bottle with a magnetic stirrer was charged with 5.00 g MeFBSE-MDI-HEA (6.920 mmol), 0.52 g EOSH (2.308 mmol), 26.92 g ethyl acetate and 0.064 g "VAZO-67". The solution was bubbled with nitrogen for two minutes. The sealed bottle was put in a 70° C. oil bath with magnetic stirring for 24 hours. The resulting solution showed precipitation at room temperature. Addition of 5.0 g DMF gave a clear solution.

Example 41

Preparation of MeFBSE-MDI-HEA/EOSH; 6.0/1.0

A 125 mL bottle with a magnetic stirrer was charged with 5.01 g MeFBSE-MDI-HEA (6.934 mmol), 0.72 g EOSH (1.154 mmol), 26.96 g ethyl acetate and 0.055 g "VAZO-67". The solution was bubbled with nitrogen for two minutes. The sealed bottle was put in a 70° C. oil bath with magnetic stirring for 24 hours. The resulting solution showed precipitation at room temperature. Addition of 5.0 g DMF gave a clear solution.

Example 42

Preparation of MeFBSE-MDI-HEA/EOSH; 8.3/1

A 125 mL bottle with a magnetic stirrer was charged with 5.01 g MeFBSE-MDI-HEA (6.925 mmol), 0.52 g EOSH (0.833 mmol), 26.60 g ethyl acetate and 0.054 g "VAZO-67". The solution was bubbled with nitrogen for two minutes. The sealed bottle was put in a 70° C. oil bath with magnetic stirring for 24 hours. The resulting solution showed precipitation at room temperature. Addition of 5.0 g DMF gave a clear solution.

Example 43

Preparation of $H(MeFBSE-MDI-HEA)_4-SC_{12}H_{25}$

A 125 mL bottle with a magnetic stirrer was charged with 4.99 g MeFBSE-MDI-HEA (6.9078 mmol), 0.35 g DDSH (1.729 mmol), 11.94 g ethyl acetate and 0.055 g "VAZO-67". The solution was bubbled with nitrogen for two minutes. The sealed bottle was put in a 70° C. oil bath and polymerized with a magnetic stirring for 24 hours. The resulting solution had precipitated white solid. Addition of 5 g DMF gave a clear solution.

Example 44

Preparation of $H(MeFBSE-MDI-HEA)_8-SC_{12}H_{25}$

In a 125 mL bottle with a magnetic stirrer was charged with 5.02 g MeFBSE-MDI-HEA (6.940 mmol), 0.17 g DDSH (0.840 mmol), 12.0 g ethyl acetate and 0.050 g "VAZO-67". The solution was bubbled with nitrogen for two minutes. The sealed bottle was put in a 70° C. oil bath and polymerized with a magnetic stirring for 24 hours. The resulting solution had precipitated white solid. Addition of 5 g DMF turned the solution clear (22.2% solid).

TABLE 4

Examples 40–44

| Ex. | Fluoroacrylate/Comonomer Composition (molar ratio) | Contact Angle in degrees Advancing (Receding) | |
|---|---|---|---|
| | | Water | Hexadecane |
| 40 | MeFBSE-MDI-HEA (3.0) EOSH (1.0) | 129(97) | 81(65) |
| 41 | MeFBSE-MDI-HEA (6.0) EOSH (1.0) | 129(98) | 82(67) |
| 42 | MeFBSE-MDI-HEA (8.3) EOSH (1.0) | 131(111) | 81(67) |
| 43 | MeFBSE-MDI-HEA (4.0) DDSH (1.0) | 130(115) | 80(69) |
| 44 | MeFBSE-MDI-HEA (8.0) DDSH (1.0) | 128(115) | 80(69) |

Example 45

Preparation of MeFBSE-MDI-HEA/methacryloxy propyl polydimethyl silicone, 80/20 graft copolymer A 125 ml bottle was charged with 2.0 g MeFBSE-MDI-HEA, 0.5 g methacryloxy propyl polydimethyl silicone (available from Shin Etsu Chemical Co, Tokyo), 14.4 g ethyl acetate and 26 mg "Vazo 67". The resulting mixture was purged with nitrogen for two minutes, and the bottle was sealed and kept in a rotating water bath at 70° C. for 24 hours. To the resulting cloudy solution was added 5.0 g DMF. Size exclusion chromatography (SEC) analysis showed 90.4% conversion with Mn=13,200; Mw=28,800 and Mw/Mn=2.2.

Example 46

Preparation of MeFBSE-MDI-HEA/methacryloxy propyl polydimethyl silicone, 60/40 graft copolymer A 125 ml bottle was charged with 1.51 g MeFBSE-MDI-HEA, 1.01 g methacryloxy propyl polydimethyl silicone (available from Shin Etsu Chemical Co., Tokyo), 14.4 g ethyl acetate and 22 mg "Vazo 67". The resulting mixture was purged with nitrogen for two minutes, and the bottle was sealed and kept in a rotating water bath at 70° C. for 24 hours. To the resulting cloudy solution was added 5.0 g DMF. SEC analysis showed 85.4% conversion with Mn=14,400; Mw=36,300 and Mw/Mn=2.5.

TABLE 5

Examples 45–46

| Ex. | Fluoroacrylate/Comonomer Composition (molar ratio) | Contact Angle in degrees Advancing (Receding) | |
|---|---|---|---|
| | | Water | Hexadecane |
| 45 | MeFBSE-MDI-HEA (80) methacryloxy propyl polydimethyl silicone (20) | 118(99) | 71(54) |
| 46 | MeFBSE-MDI-HEA (60) methacryloxy propyl polydimethyl silicone (40) | 127(107) | 80(62) |

Example 47

Release Coatings

The copolymer of Example 27 was diluted to 5% solids with toluene. The solution was then coated with a #6 wire wound (Mayer) rod onto a 1.6 mil primed polyester terephthalate film. The coated film was attached to a fiberboard frame and dried for 15 minutes at 65° C.

The test method used to evaluate the release coatings was a modification of the industry standard peel adhesion test used to evaluate pressure sensitive adhesive coated materials. The standard test is described in detail in various publications of the American Society for Testing and Materials (ASTM), Philadelphia, Pa., and the Pressure Sensitive Tape Council (PSTC), Glenview, Ill. The modified standard method is described in detail below. The reference source of the standard test method is ASTM D3330-78 PSTC-1 (11/75)

2.54 cm by 15.24 cm strips of Scotch® Performance Masking Tape 233+ (available from 3M Company, St. Paul, Minn.) were rolled down onto the coated polyester film with a 2.04 kg rubber roller. The laminated samples were then aged 1 week at 22° C. and 50% relative humidity or 16 hours at 65° C. Prior to testing, the heat-aged samples were equilibrated to 22° C. and 50% relative humidity for 24 hours.

Release testing was conducted by mounting the masking tape/coated film laminate to the stage of an Instrumentors, Inc. slip/peel tester (model 3M90) with double coated tape. The force required to remove the masking tape at 180 degrees and 228.6 cm/minute was then measured. Tape re-adhesions were also measured by adhering the freshly peeled masking tape to a clean glass plate and measuring the peel adhesion in normal fashion using the same Instrumentors slip/peel tester indicated above, again peeling at 228.6 cm/min and at a 180 degree peel angle. The results of these peel tests are shown in Table 6.

Comparative Example 13 (C13)

Release Coating Comprising MeFOSEA/MMA/St/AA, 60/16/15/9

120 g MeFOSEA ($C_8F_{17}SO_2N(CH_3)CH_2CH_2OC(O)CH=CH_2$) was charged to a 2 liter reaction flask equipped with a heating mantle, a condenser, $N_2$ inlet and an agitator. The flask was heated to 70° C. to melt MeFOSEA. Then a premix of 32 g methyl methacrylate, 30 g styrene, 18 g acrylic acid, 6.0 g Rhodacal DS-10 surfactant, 5.71 g Zonyl™ FSP (DuPont) surfactant and 600 g deionized water was charged to the flask. The resulting milky solution was purged with $N_2$ for 5 minutes at 1 liter per minute and heated to 50° C. followed by addition of initiator, 0.3 g $K_2S_2O_8$ (potassium persulfate), dissolved in 10 g water. The reaction mixture was heated at 50° C. for 1 hr. The temperature was raised to 75° C. and the reaction was carried out for additional 5 hours. The resulting emulsion was cooled down to room temperature. The % solids were measured to be 26%, resulting in 99.5% conversion. Release coatings were prepared and tested as described in Example 45. The results are shown in Table 6 below.

TABLE 6

Example 47 and Comparative Example C13

| Sample | Example 47 Peel Force from Release Coating (g/cm) | Example C13 Peel Force from Release Coating (g/cm) | Example 47 Readhesion Peel Force from Glass (g/cm) | Example C13 Readhesion Peel Force from Glass (g/cm) |
|---|---|---|---|---|
| 7 days @ 22° C. | 122.8 | 200.9 | 625.0 | 468.7 |
| 16 hrs @ 65° C. | 267.8 | 401.8 | 502.2 | 390.6 |

Example 48

The copolymer of Example 45 was coated and tested according to the methods described in Example 47 with the exception that SCOTCH MAGIC TAPE 810 (Available from 3M Company) was used in place of SCOTCH PERFORMANCE MASKING TAPE 233+. The results are shown in Table 7 below

TABLE 7

| Example 48 | Peel Force from Release Coating (g/cm) | Readhesion Peel Force from Glass (g/cm) |
|---|---|---|
| 7 days @ 22° C. | 95.2 | 357.0 |
| 16 hrs @ 65° C. | 148.8 | 312.5 |

Example 49

Release coating of Example 47 was prepared and tested according to the methods described above using a silicone polyurea pressure sensitive adhesive that was prepared and coated as described in U.S. Pat. No. 6,569,521 (see Example 31). The peel force from the release coating and subsequent readhesion to glass was measured. Three aging conditions were evaluated: 7 days at 22° C. (50% relative humidity), 7 days at 50° C. and 3 days at 70° C. The results are shown in Table 8 below

TABLE 8

| Example 49 | Peel Force from Release Coating (g/cm) | Readhesion Peel Force from Glass (g/cm) |
|---|---|---|
| 7 days @ 22° C. | 11.8 | 546.8 |
| 7 days @ 50° C. | 18.1 | 580.3 |
| 3 days @ 70° C. | 27.2 | 580.3 |

We claim:

1. A fluoroacrylate monomer consisting of the reaction product of:
   (a) at least one fluorochemical alcohol represented by the formula:

$C_nF_{2n+1}$—X—OH wherein:

n = 1 to 5,

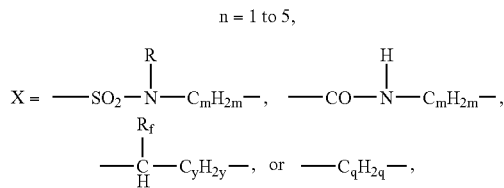

R=hydrogen or an alkyl group of 1 to 4 carbon atoms,
   m=2 to 8,
   $R_f$=$C_nF_{2n+1}$,
   y=0 to 6, and
   q=1 to 8;
   (b) at least one unbranched symmetric diisocyanate; and
   (c) at least one hydroxy-terminated alkyl (meth)acrylate or 2-fluoroacrylate monomer having 2 to about 30 carbon atoms in its alkylene portion.

2. The fluoroacrylate monomer of claim 1 wherein X is

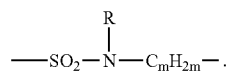

3. The fluoroacrylate monomer of claim 2 wherein R is a methyl group.

4. The fluoroacrylate monomer of claim 3 wherein m is from 2 to 4.

5. The fluoroacrylate monomer of claim 1 wherein n is from 1 to 4.

6. The fluoroacrylate monomer of claim 5 wherein n is 4.

7. The fluoroacrylate monomer of claim 6 wherein said fluorochemical alcohol is selected from the group consisting of $C_4F_9SO_2NCH_3(CH_2)_2OH$, $C_4F_9SO_2NCH_3(CH_2)_4OH$, and $C_4F_9(CH_2)_2OH$.

8. The fluoroacrylate monomer of claim 7 wherein said fluorochemical alcohol is $C_4F_9SO_2NCH_3(CH_2)_2OH$.

9. The fluoroacrylate monomer of claim 1 wherein said unbranched symmetric diisocyanate is selected from the group consisting of 4,4'-diphenylmethane diisocyanate, 1,6-hexamethylene diisocyanate, and 1,4-phenylene diisocyanate.

10. The fluoroacrylate monomer of claim 9 wherein said unbranched symmetric diisocyanate is 4,4'-diphenylmethane diisocyanate.

11. The fluoroacrylate monomer of claim 1 wherein said hydroxy-terminated alkyl (meth)acrylate or 2-fluoroacrylate monomer has between about 2 and about 12 carbon atoms in its alkylene portion.

12. The fluoroacrylate monomer of claim 1 wherein said hydroxy-terminated alkyl (meth)acrylate or 2-fluoroacrylate monomer is a hydroxy-terminated alkyl acrylate monomer.

13. The fluoroacrylate monomer of claim 12 wherein said hydroxy-terminated alkyl acrylate monomer is selected from the group consisting of hydroxy ethyl acrylate, hydroxy butyl acrylate, hydroxy hexyl acrylate, hydroxy decyl acrylate, and hydroxy dodecyl acrylate.

14. The fluoroacrylate monomer of claim 1 wherein the fluoroacrylate monomer is the reaction product of:
   (a) $C_4F_9SO_2NCH_3(CH_2)_2OH$,
   (b) 4,4'-diphenylmethane diisocyanate, and
   (c) hydroxy butyl acrylate or hydroxy ethyl acrylate.

15. A fluorinated acrylic polymer comprising repeating units of the fluoroacrylate monomer of claim 1 and repeating units derived from one or more nonfunctional comonomers.

16. A coating composition comprising a solvent and the fluorinated acrylic polymer of claim 15.

17. An article comprising a substrate having one or more surfaces coated with the coating composition of claim 16.

18. The article of claim 17 wherein said substrate is a hard substrate or a fibrous substrate.

19. A release coating composition comprising a solvent and the fluorinated acrylic polymer of claim 15.

20. An article comprising a substrate having one or more surfaces coated with the release coating composition of claim 19.

21. The fluoroacrylate monomer of claim 1 wherein the alkylene portion of the hydroxy-terminated alkyl (meth)acrylate or 2-fluoroacrylate monomer is represented by the following general formula:

—$(C_pH_{2p})$— wherein p=2 to 30.

22. The fluoroacrylate monomer of claim 21 wherein said hydroxy-terminated alkyl (meth)acrylate or 2-fluoroacrylate monomer is a hydroxy-terminated alkyl acrylate monomer.

23. The fluoroacrylate monomer of claim 22 wherein said at least one unbranched symmetric diisocyanate comprises an aromatic diisocyanate, and p=2.

24. The fluoroacrylate monomer of claim 1 wherein the fluoroacrylate monomer is represented by the following general formula:

$C_nF_{2n+1}$—X—OC(O)NH-A-HNC(O)O—$(C_pH_{2p})$(O)COC(R')=$CH_2$ wherein:
   A=an unbranched symmetric alkylene group, arylene group, or aralkylene group,
   p=2 to 30, and
   R'=H, $CH_3$, or F.

25. The fluoroacrylate monomer of claim 24 wherein A is an aromatic group, p=2, and R'=H.

26. The fluoroacrylate monomer of claim 25 wherein said n is 1 to 4.

27. The fluoroacrylate monomer of claim 25 wherein X is

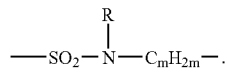

28. The fluoroacrylate monomer of claim 27 wherein R is CH$_3$ and m is from 2 to 4.

29. The fluoroacrylate monomer of claim 27 wherein A is selected from the group consisting of

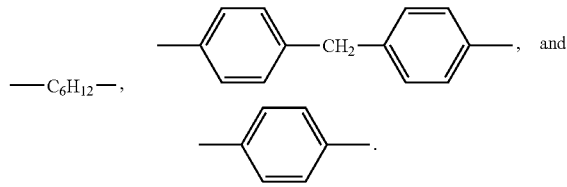

30. The fluoroacrylate monomer of claim 29 wherein A is

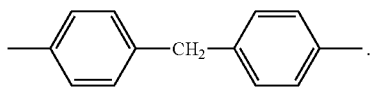

31. A fluorinated acrylic polymer comprising repeating units of the fluoroacrylate monomer of claim 25.

32. A coating composition comprising a solvent and the fluorinated acrylic polymer of claim 31.

33. An article comprising a substrate having one or more surfaces coated with the coating composition of claim 32.

34. The fluoroacrylate monomer of claim 14 wherein the fluoroacrylate monomer is represented by the following general formula:

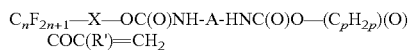

wherein:
n is 4,

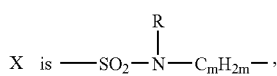

R is methyl,
m is 2,

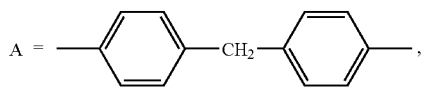

p=2 or 4, and
R'=H.

35. A fluoroacrylate monomer consisting of the reaction product of:
(a) at least one fluorochemical alcohol represented by the formula:

wherein:

n = 1 to 5,

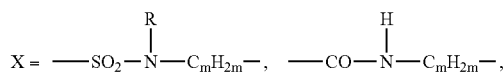

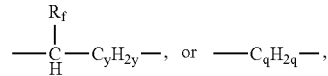

R=hydrogen or an alkyl group of 1 to 4 carbon atoms,
m=2 to 8,
R$_f$=C$_n$F$_{2n+1}$,
y=0 to 6, and
q=1 to 8;
(b) at least one unbranched symmetric diisocyanate; and
(c) at least one hydroxy-terminated alkyl acrylate or 2-fluoroacrylate monomer having 2 to about 30 carbon atoms in its alkylene portion.

36. The fluoroacrylate monomer of claim 35 wherein the fluoroacrylate monomer is represented by the following general formula:

wherein:
A=an unbranched symmetric alkylene group, arylene group, or aralkylene group,
p=2 to 30, and
R'=H or F.

37. A fluorinated acrylic polymer comprising repeating units of the fluoroacrylate monomer of claim 35.

38. A fluoroacrylate monomer comprising of the reaction product of:
(a) at least one fluorochemical alcohol represented by the formula:

wherein:

n = 1 to 5,

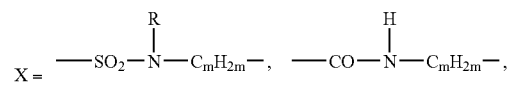

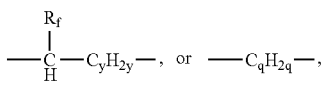

R=hydrogen or an alkyl group of 1 to 4 carbon atoms,
m=2 to 8,
R$_f$=C$_n$F$_{2n+1}$,
y=0 to 6, and
q=1 to 8;
(b) at least one unbranched symmetric diisocyanate; and
(c) at least one hydroxy-terminated alkyl (meth)acrylate or 2-fluoroacrylate monomer having 2 to about 30 carbon atoms in its alkylene portion;
wherein said fluoroacrylate monomer does not comprise a fluorine atom other than fluorine atoms of component (a), the single fluorine atom of component (c), or both.

39. The fluoroacrylate monomer of claim 38 wherein the fluoroacrylate monomer is represented by the following general formula:

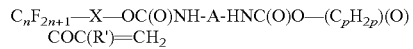

wherein:

A=an unbranched symmetric alkylene group, arylene group, or aralkylene group,
p=2 to 30, and
R'=H or F.

40. A fluorinated acrylic polymer comprising repeating units of the fluoroacrylate monomer of claim 39.

41. A fluoroacrylate monomer comprising of the reaction product of:
(a) at least one fluorochemical alcohol represented by the formula:

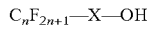

wherein:

n = 1 to 5,

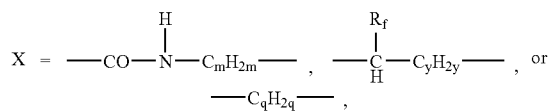

R=hydrogen or an alkyl group of 1 to 4 carbon atoms,
m=2 to 8,
$R_f=C_nF_{2n+1}$,
y=0 to 6, and
q=1 to 8;
(b) at least one unbranched symmetric diisocyanate; and
(c) at least one hydroxy-terminated alkyl (meth)acrylate or 2-fluoroacrylate monomer having 2 to about 30 carbon atoms in its alkylene portion;
wherein said fluoroacrylate monomer does not comprise a fluorine atom other than fluorine atoms of component (a), the single fluorine atom of component (c), or both.

42. The fluoroacrylate monomer of claim 41 wherein the fluoroacrylate monomer is represented by the following general formula:

wherein:
A=an unbranched symmetric alkylene group, arylene group, or aralkylene group,
p=2 to 30, and
R'=H or F.

43. The fluoroacrylate monomer of claim 42 wherein R'=H.

* * * * *